United States Patent [19]

Hsiung et al.

[11] Patent Number: 4,795,706
[45] Date of Patent: Jan. 3, 1989

[54] NOVEL EXPRESSION CONTROL SEQUENCES

[75] Inventors: Hansen M. Hsiung; Dennis P. Smith, both of Indianapolis, Ind.

[73] Assignee: Eli Lilly and Company, Indianapolis, Ind.

[21] Appl. No.: 697,093

[22] Filed: Jan. 31, 1985

[51] Int. Cl.⁴ .............. C12N 15/00; C12N 1/20; C12P 21/00; C07H 15/12

[52] U.S. Cl. .................. 435/172.3; 435/68; 435/320; 435/252.33; 536/27; 935/29; 935/41; 935/43; 935/56; 935/73

[58] Field of Search .............. 435/68, 172.3, 317, 435/253, 320; 536/27; 935/29, 41, 43, 56, 73

[56] References Cited

U.S. PATENT DOCUMENTS 4,643,969 2/1987 Inouye et al. .............. 435/68

OTHER PUBLICATIONS

Nishi et al. Agric. Biol. Chem. 48(3): 699–675. 1984.
Nakamura et al., 1982, Journal of Molecular and Applied Genetics 1: 289.
Tacon et al., 1983, Gene 23: 255.
Amann et al., 1983, Gene 25: 167.
Hawley and McClure, 1983, Nucleic Acids Research 11(8): 2237.

Primary Examiner—Charles F. Warren
Assistant Examiner—David T. Fox
Attorney, Agent, or Firm—Gerald V. Dahling; Leroy Whitaker

[57] ABSTRACT

The present invention comprises novel expression control sequences that promote transcription of DNA. The novel sequences have been positioned for expression of structural genes encoding bovine growth hormone derivatives on recombinant DNA expression vectors. The novel expression control sequences function in both Gram-positive and Gram-negative organisms and can be constructed by either DNA synthesizing instruments or by conventional modified phosphotriester methodology.

20 Claims, 11 Drawing Sheets

Restriction Site and Function Map of
Plasmid pCZ101
(10.8 kb)

Restriction Site and Function Map of
Plasmid pCLTbGH51
(9.9 kb)**

Restriction Site and Function Map of
Plasmid pCLTbGH29
(9.9 kb)

NOVEL EXPRESSION CONTROL SEQUENCES

The present invention provides novel DNA compounds useful in recombinant DNA technology. The novel compounds, called expression control sequences, promote transcription of DNA. The disclosed compounds comprise sequences known to enhance translation of mRNA in *E. coli* or, since translational activating sequences vary from organism to organism, are readily modified to comprise translational activating sequences from any organism. The present invention also provides several unique expression vectors, constructed so that the novel expression control sequences drive transcription and expression of DNA encoding bovine growth hormone (bGH) derivatives.

Transformants harboring these unique expression vectors express the bGH derivatives at levels approaching 30% of the total cell protein. The present control sequences and expression vectors are extremely versatile, possess a variety of conveniently placed restriction sites, and allow for easy construction of derivative vectors comprising the novel expression control sequences and any structural gene of interest.

Although over 150 *E. coli* expression control sequences have been characterized, only a few have the properties needed for use in biotechnology. These properties include the ability to drive transcription of high levels of mRNA and the ability to function in both Gram-positive as well as Gram-negative organisms. Ideally, the expression control sequences will also be portable and regulatable. Few, if any, of the presently known promoters possess all of these properties. Thus, a list of expression control sequences of significant value in biotechnology might be limited to the lpp, lac, trp, tac, and lambda pL promoters. The present expression control sequences significantly expand this list.

The present expression control sequences result from efforts to create a hybrid lpp-trp expression control sequence. Merely fusing the −30 to −50 region of the lpp control sequence to the −1 to −30 region of the trp control sequence led to poor results. Derivatives of this initial construct were, however, very effective expression control sequences and constitute the present invention. The present compounds can be used to transcribe any DNA and are particularly useful for transcribing and expressing structural genes.

For purposes of the present invention, as disclosed and claimed herein, the following terms are as defined below.

Expression Control Sequence—any DNA sequence that directs or provides for the transcription of DNA into RNA.

Functional Polypeptide—a recoverable bioactive heterologous or homologous polypeptide or precursor, a recoverable bioactive polypeptide comprising a heterologous polypeptide and a portion or whole of a homologous polypeptide, or a recoverable bioinactive fusion polypeptide comprising a heterologous polypeptide and a bio-inactivating polypeptide which can be specifically cleaved.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which an expression control sequence has been incorporated.

Replicon—A DNA sequence that controls and allows for replication of a plasmid or other vector.

Restriction Fragment—any linear DNA sequence generated by the action of one or more restriction enzymes.

Sensitive Host Cell—a host cell that cannot grow in the presence of a given antibiotic without a DNA segment that confers resistance thereto.

Structural Gene—any DNA sequence that encodes a functional polypeptide, inclusive of that DNA encoding the start and stop codons.

Transformation—the introduction of DNA into a recipient host cell that changes the genotype of the recipient cell.

Transformant—a recipient host cell that has undergone transformation.

Translational Activating Sequence—any DNA sequence, inclusive of that encoding a ribosome binding site, that provides for the translation of a mRNA transcript into a peptide or polypeptide.

DETAILED DESCRIPTION OF THE INVENTION

The expression control sequences of the present invention are:

(A) 5'-AATTCCATCAAAAAAATATTGACAACATATCATCGAACTAGTTAACTAGTAC
    |||||||||||||||||||||||||||||||||||||||||||||||||||
    3'-GGTAGTTTTTTTATAACTGTTGTATAGTAGCTTGATCAATTGATCATG

GCAAGTTCACGT-3'
||||||||||||
CGTTCAAGTGCAGATC-5'

(B) 5'-AATTCCATCAAAAAAATATTGACAACATATCATCGAACTAGTTAACTAGTACGC
    ||||||||||||||||||||||||||||||||||||||||||||||||||||||
    3'-GGTAGTTTTTTTATAACTGTTGTATAGTAGCTTGATCAATTGATCATGCG

AAGTTCACGTAAAAAGGGTAT-3'
|||||||||||||||||||||
TTCAAGTGCATTTTTCCCATAGC-5'

(C) 5'-AATTCCATCAAAAAAATATTGACAACATATCATCGAACTAGTATAATAGTACGCA
    |||||||||||||||||||||||||||||||||||||||||||||||||||||||
    3'-GGTAGTTTTTTTATAACTGTTGTATAGTAGCTTGATCATATTATCATGCGT

AGTTCACGT-3'
|||||||||
TCAAGTGCAGATC-5'

(D) 5'-AATTCCATCAAAAAAATATTGACAACATATCATCGAACTAGTATAATAGTACGCA
    |||||||||||||||||||||||||||||||||||||||||||||||||||||||
    3'-GGTAGTTTTTTTATAACTGTTGTATAGTAGCTTGATCATATTATCATGCGT

```
AGTTCACGTAAAAAGGGTAT-3'
|||||||||||||||||||||
TCAAGTGCATTTTTCCCATAGC-5'
``` wherein A is deoxyadenyl, G is deoxyguanyl, C is deoxycytidyl, and T is thymidyl.

The novel expression control sequences depicted above can be synthesized from single stranded deoxyoligonucleotides by procedures well known in the art. The single stranded deoxyoligonucleotides can be synthesized with commercially available instruments, such as the 380A DNA Synthesizer marketed by Applied Biosystems (850 Lincoln Centre Drive, Foster City, CA 94404), which utilizes phosphoramidite chemistry. Other procedures for synthesizing DNA are also known in the art. The conventional modified phosphotriester method of synthesizing single stranded DNA is described in Itakura et al., 1977, Science 198: 1056 and in Crea et al., 1978, Proc. Nat. Acad. Sci. USA 75: 5765. In addition, an especially preferred method of synthesizing DNA is disclosed in Hsiung et al., 1983, Nucleic Acid Research 11: 3227 and Narang et al., 1980, Methods in Enzymology 68: 90.

The present expression control sequences can be used to drive transcription of any correctly positioned DNA sequence. Most often, the expression control sequence will be positioned to transcribe a structural gene encoding a functional polypeptide, but the present sequences would function equally well in vectors designed to express an RNA of research or commercial interest. A variety of expression vectors have been constructed that comprise the present control sequences positioned for expression of structural genes encoding bovine growth hormone (bGH) derivatives. When these vectors are transformed into an appropriate host, such as E. coli K12 RV308 (NRRL B-15624), and the resulting transformed cell is cultured at 37° C., the encoded bGH derivative is expressed at levels approaching 30% of the total cell protein. These bGH derivatives can be used to increase feed efficiency and milk production in cattle, as disclosed in U.S. patent application Ser. No. 6,634,920, filed July 26, 1984. Thus, the present invention comprises novel expression control sequences, methods for the production of functional polypeptides, recombinant DNA cloning and expression vectors, and useful transformants constructed with the vectors.

Some of the starting materials of the present invention, specifically plasmid pCZ101, were also disclosed in the above-named application. A brief description of the construction of plasmid pCZ101 is provided below; the construction is also described in the Example section herein.

The plasmid pCZ101 starting material is ~10.8 kb and is constructed by ligating the ~0.6 kb XbaI-BamHI fragment of plasmid pNM789B into similarly digested plasmid pIM-I'-A3. The latter plasmid, which contains the transcriptional and translational activating sequence of the E. coli lipoprotein gene as well as a runaway replicon, can be obtained from E. coli K12 RV308/pIM-I'-A3, a strain deposited and made part of the permanent stock culture collection of the Northern Regional Research Laboratory, Peoria, Ill. The strain is available as a preferred source and stock reservoir of the plasmid under the accession number NRRL B-15733.

The plasmid pNM789B starting material is derived from plasmid pKEN111 in accordance with the steps illustrated and described in FIGS. 1–8 and Example 1 below. Plasmid pKEN111 can be obtained from E. coli K12 CC620/pKEN111, a strain deposited and made part of the permanent stock culture collection of the Northern Regional Research Laboratory, Peoria, Ill. The strain is available as a preferred source and stock reservoir of the plasmid under the accession number NRRL B-15011. Plasmid pNM789B also contains the transcriptional and translational activating sequence of the E. coli lipoprotein gene and, in addition, the coding sequence, including an appropriately positioned translational stop signal, for a fusion protein comprising bGH and a nine member polypeptide at the bGH aminoterminus. Ligation of the fusion protein-coding sequence, containing in the XbaI-BamHI fragment, to appropriately cleaved plasmid pIM-I'-A3 results in the aforementioned plasmid pCZ101 starting material. A restriction site and function map of plasmid pCZ101 is presented in FIG. 9 of the accompanying drawings.

Plasmid pCZ101 was further modified by deleting the ~900 bp BstEII restriction fragment to yield plasmid pCZ103. The ~9.3 kb EcoRI-BamHI and ~0.6 BamHI-HgiAI restriction fragments of plasmid pCZ103 were ligated to the linker sequence:

```
5'-CGATA ATG GAT TTT CCG GCT ATG TCT CTG TCC GGC CTG TTT GCC
     ||| ||| ||| ||| ||| ||| ||| ||| ||| ||| ||| ||| ||| |||
3'-TAT TAC CTA AAA GGC CGA TAC AGA GAC AGG CCG GAC AAA CGG

AAC GCT GTGCT-3'
||| ||| |
TTG CGA C-5'      ,
``` wherein A is deoxyadenyl, G is deoxyguanyl, C is deoxycytidyl, and T is thymidyl, along with expression control sequence B or D above to form illustrative plasmids pCLTbGH51 and pCLTbGH64, respectively. Cells transformed by plasmids pCLTbGH51 and pCLTbGH64 express MET-ASP-bGH, wherein MET is methionine, ASP is aspartic acid, and bGH is the natural amino acid sequence of bovine growth hormone beginning with the amino-terminal (first) phenylalanine. A restriction site and function map of plasmid pCLTbGH51 is presented in FIG. 10 of the accompanying drawings.

The ~9.3 kb BamHI-EcoRI and ~0.6 kb BamHI-HgiAI restriction fragments of plasmid pCZ103 were ligated to the linker sequence:

```
5'-CTAGAGGGTATTAATA ATG TTT CCA GCT ATG TCT CTA TCT GGT CTG TTT
   ||||||||||||||||  ||| ||| ||| ||| ||| ||| ||| ||| ||| ||| |||
3'-TCCCATAATTAT TAC AAA GGT CGA TAC AGA GAT AGA CCA GAC AAA
```

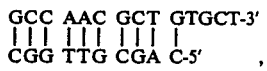

```
GCC AAC GCT GTGCT-3'
||| ||| ||| |
CGG TTG CGA C-5'
``` wherein A is deoxyadenyl, G is deoxyguanyl, C is deoxycytidyl, and T is thymidyl, along with expression control sequence A or C above to form illustrative plasmids pCLTbGH29 and pCLTbGH37, respectively. Cells transformed by plasmids pCLTbGH29 and pCLTbGH37 express MET-bGH, wherein MET is methionine and bGH is the natural amino acid sequence of bovine growth hormone beginning with the amino-terminal (first) phenylalanine. A restriction site and function map of plasmid pCLTbGH29 is presented in FIG. 11 of the accompanying drawings.

In the specific embodiments herein described, plasmid replication is determined by a thermoinducible runaway replicon disclosed in both GB patent publication No. 1,557,774 and Uhlin et al., 1979, Gene 6: 91. At temperatures below 30° C., especially 25° C., the replicon maintains a relatively low copy number of about 10–15 copies per cell. When the temperature is raised to 37° C., copy number control is lost and plasmids containing the replicon amplify to 1000–2000 copies per cell. The particular runaway replicon exemplified herein is contained in the previously described plasmid pIM-I'-A3 starting material. Skilled artisans will understand that the present invention is not limited to the use of any particular runaway replicon or copy number mutant. Other inducible runaway or high copy number replicons can be obtained by appropriate selection or can be constructed in accordance with the procedure disclosed in International Publication No. WO82/02901.

The present expression control sequences can also be used on vectors that lack a runaway replicon, such as plasmids pBR322, pBR328, pBR329, pACYC184, pKO1, and pKC7. Such replicons can be used to construct expression vectors that are also within the scope of the present invention.

The cloning of foreign genes into vectors comprising the present expression conttol sequences and a runaway replicon results, upon induction and loss of copy number control, in a greatly increased rate of protein synthesis and the concomitant formation of a species of intracellular proteinaceous granule. The granules of the present invention are highly homogeneous with the desired protein product comprising at least 50% and often exceed 80% of the granule.

Many modifications and variations of the present illustrative DNA sequences and plasmids are possible. For example, the degeneracy of the genetic code allows for the substitution of nucleotides throughout polypeptide coding regions as well as for translational stop signals. Thus any number of possible DNA sequences that code for bGH can be deduced from the known amino acid sequence of bGH and can be constructed by following conventional synthetic procedures.

Furthermore, other structural genes of interest can be substituted for the bGH derivative structural genes specifically exemplified. In this manner, the present expression control sequences can be used to express structural genes such as those encoding natural bovine growth hormone, avian growth hormone, human growth hormone, growth hormone releasing factor, proinsulin, insulin A chain, insulin B chain, Factor VIII, tissue plasminogen activator, IGFI, IGFII, interleukin I, interleukin II, a hormone, and an enzyme.

However, nucleotide triplets should be chosen in accordance with known principles and extrapolations reviewed in Zuker and Stiegler, 1981, Nucleic Acids Research 9(1): 133, to avoid generating complementary bases in mRNA. Hydrogen bonding (pairing) between such complementary bases results in stem and loop configurations and folding that reduce the efficiency of translation. Skilled artisans will understand that all of the modifications and variations disclosed above can be conventionally synthesized in substantial accordance with the synthetic methods previously cited. Therefore, the present invention is in no way limited to the DNA sequences and plasmids specifically exemplified.

The present expression control sequences, as exemplified above, have EcoRI and XbaI or EcoRI and ClaI overlaps located at the ends of the molecule. These overlaps facilitate ligation but do not contribute to the transcription or translational activating activity of the sequences. Thus, these overlaps can be altered, or the entire expression control sequence constructed, to facilitate ligation into restriction enzyme recognition sites other than EcoRI, XbaI, or ClaI. Therefore, the present expression control sequences are in no way limited to the particular overlaps exemplified herein.

The expression control sequences and vectors of this invention can be applied to a wide range of host organisms, such as, for example, Gram-negative prokaryotic organisms *Escherichia coli*, *E. coli* K12, *E. coli* K12 RV308, *E. coli* K12 HB101, *E. coli* K12 C600, *E. coli* K12 C600 $R_k$-$M_k$-, *E. coli* K12 RR1, *E. coli* K12 MM294, and the like or Gram-positive organisms such as Streptomyces and Bacillus. Although all of the embodiments of the present invention are useful, some of the vectors and transformants are preferred. Preferred vectors include pCLTbGH29, pCLTbGH37, pCLTbGH51, and pCLTbGH64 and preferred transformants include *E. coli* K12 RV308/pCLTbGH29, *E. coli* K12 RV308/pCLTbGH37, *E. coli* K12 RV308/pCLTbGH51, and *E. coli* K12 RV308/pCLTbGH64.

Those skilled in the art will recognize that the expression vectors of this invention are used to transform suitable host organisms such that a bovine growth hormone derivative product is expressed using standard fermentation conditions. The product, expressed as a highly homogeneous granule and isolated by routine methods for the resulting fermentation broth, is useful for increasing milk production and for generally stimulating growth in cattle. Modes of use, administration and suitable dosages for cattle are known and disclosed in European Patent Office Publication No. 0085036, pages 7–9, incorporated herein by reference. The following examples further illustrate the invention disclosed herein. Both an explanation of and the actual procedures for constructing the invention are described where appropriate.

EXAMPLE 1

Construction of Plasmid pNM789B

A. Construction of Plasmid pKEN021 and the XbaI-BamHI Fragment Thereof

The ~5.1 kb fragment produced by XbaI-BamHI cleavage of plasmid pKEN021 (106 in FIG. 3) was used as starting material. Plasmid pKEN021 is a derivative of pKEN111, (101 in FIG. 1 and further described in Lee, et al., 1981, J. Bact. 146: 861-866 and Zwiebel, et al., 1981, J. Bact. 145: 654-656), which is on deposit in E. coli CC620 (NRRL Deposit No. B-15011) and which has a ~2.8 kb fragment which contains the lipoprotein gene of E. coli. A description of this fragment is provided in Nakamura and Inouye, 1979, Cell 18: 1109-1117.

In plasmid pKEN021, the 650 bp (base pair) sequence between the unique EcoRI and SalI restriction sites of pBR322 has been replaced by sequences taken from the lipoprotein gene of E. coli. The lipoprotein gene sequence (Nakamura and Inouye, 1979) includes a 462 bp AluI fragment, upstream from the first triplet (ATG) of the lipoprotein gene that contains the promoter, the 5' untranslated region, and the ribosome binding site. A unique XbaI restriction site is located within the ribosome binding site 16 bp before the translation initiating, methionine-encoding signal. A PvuII restriction site located 105 bp upstream from the translation termination codon of the structural gene was changed to a BamHI restriction site by the addition of a synthetic DNA linker (5'-CCGGATCCGG-3', obtained from Collaborative Research). The coding sequence for the last 35 amino acids of lipoprotein, the translation termination signal, and the sequence corresponding to the 3' untranslated region of the messenger RNA follow the BamHI site. Plasmid pKEN021 also includes some 850 bp of extraneous sequences unrelated to the lipoprotein gene and located downstream of it in the E. coli chromosome. These sequences were included as a consequence of the methods and restriction enzyme sites used in the original isolation of the gene.

Figure 1:
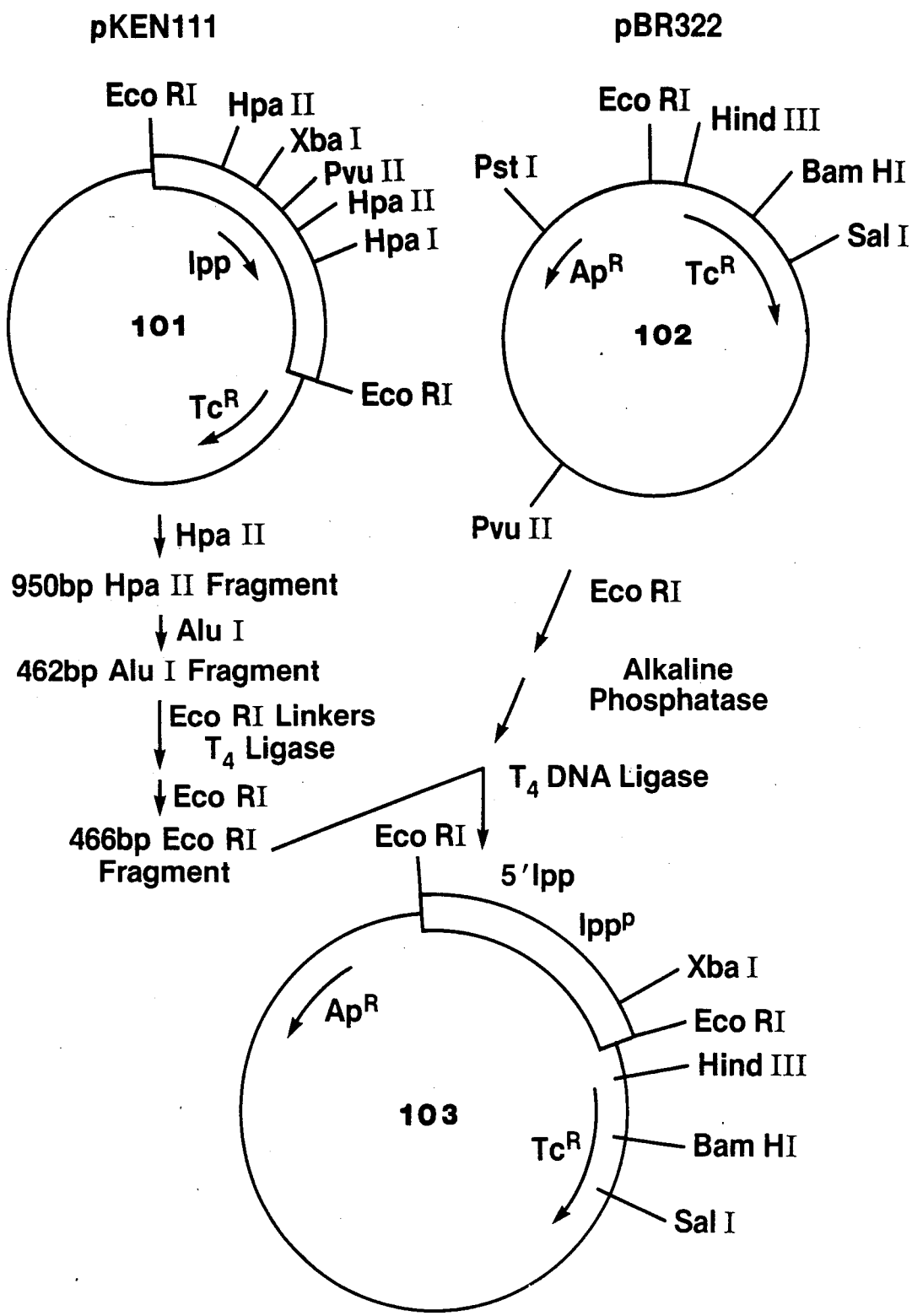
FIGS. 1–8—the construction of plasmid pNM789B.
Figure 2:
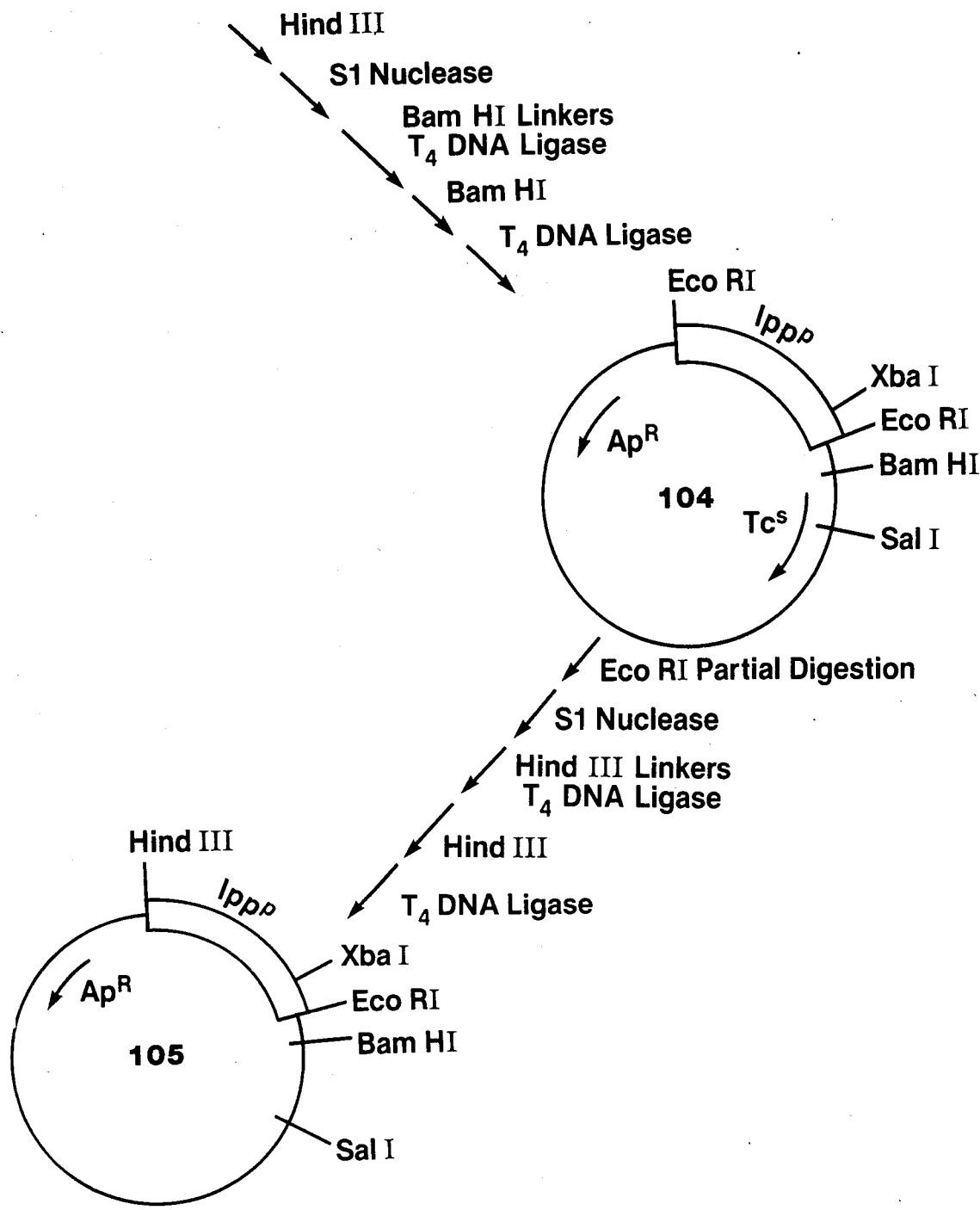
Figure 3:
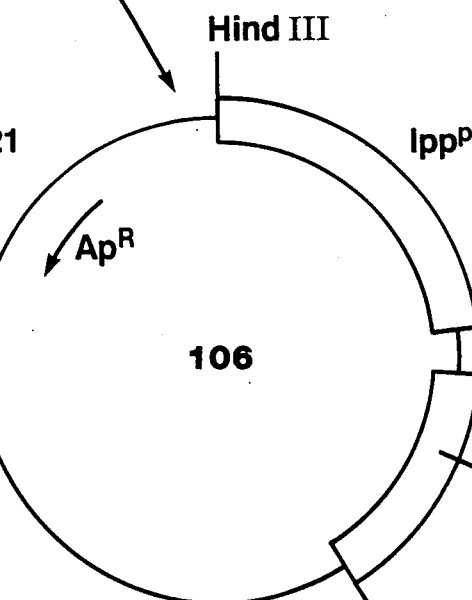
Figure 3:
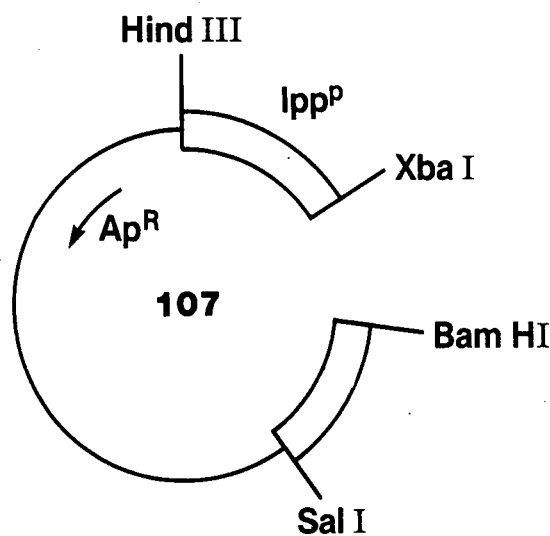

Referring to FIGS. 1, 2, and 3, plasmid pKEN021 is derived from pKEN111 in the following manner: About 50 μg of plasmid pKEN111 (101 in FIG. 1) are digested with 25 units of HpaII restriction enzyme in 300 μl of a buffer containing 20 mM Tris.HCl, pH 7.4; 10 mM MgCl$_2$; 6 mM KCl and 1 mM dithiothreitol at 37° C. for 2 hours. The mixture is extracted twice with 300 μl of a 50:50 mixture of phenol and chloroform and the recovered aqueous phase is then precipitated, after chilling to −70° C., with 2.5 volumes of ethanol and 0.1 volume of 3M sodium acetate. The DNA pellet is dissolved in 100 μl of electrophoresis buffer and fractionated on a 5 percent polyacrylamide gel (acrylamide:bis ratio is 29:1 in all gels except where noted). The gel is stained in a solution containing 0.5 μg/ml of ethidium bromide and bands are visualized under long wave-length ultraviolet light. A 950 bp band is isolated and recovered from the gel by electroelution into a dialysis bag. After phenol/CHCl$_3$ extraction and ethanol precipitation, the recovered DNA (approximately 2.5 μg) is dissolved in 25 μl of TEN (10 mM NaCl; 10 mM Tris.HCl, pH 7.4; and 1 mM sodium ethylenedinitrilotetraacetate (EDTA), pH 8.0).

About 2 μg of the 950 bp HpaII fragment are digested with AluI restriction enzyme in 200 μl of a buffer containing 50 mM NaCl, 6 mM Tris.HCl (pH 7.6), 6 mM MgCl$_2$, and 6 mM β-mercaptoethanol for 2 hours at 37° C. The DNA is fractionated on a 6 percent polyacrylamide gel and the 462 bp AluI fragment generated is recovered and purified by the method previously described. The 462 bp AluI fragment (approximately 1 μg) is dissolved in 10 μl of T4 DNA ligase buffer (50 mM Tris.HCl, pH 7.8; 10 mM MgCl$_2$; 20 mM dithiothreitol; and 1.0 mM ATP) containing 150 picomoles of phosphorylated EcoRI linker (5'-GGAATTCC-3' from Collaborative Research) and 2 units T4 DNA ligase. After incubation at 4° C. for 16 hours, the mixture is heated at 65° C. for 10 minutes and diluted to 100 μl with the addition of EcoRI buffer (100 mM Tris.HCl, pH 7.5; 50 mM NaCl; 5 mM MgCl$_2$; and 6 mM β-mercaptoethanol) and 40 units EcoRI enzyme. After 2 hours at 37° C., the sample is conventionally phenol/CHCl$_3$ extracted and ethanol precipitated.

The DNA is then dissolved in 20 μl of T4 DNA ligase buffer containing 1 unit T4 DNA ligase and 0.1 μg pBR322 (102 in FIG. 1) which has been linearized with EcoRI and then treated with alkaline phosphatase. After ligation at 4° C. for 16 hours, the resultant DNA is used to conventionally transform E. coli K12 RV308 (NRRL B-15624). Transformants are selected on agar plates containing 12 μg/ml of tetracycline and plasmids isolated from resistant colonies by the rapid alkaline extraction procedure described in Birnboim and Doly, 1979, Nucleic Acids Research 7: 1513-1523. A plasmid (103 in FIG. 1) containing a 466 bp XbaI-BamHI fragment is selected and used as the starting material for the step next described.

About two μg of this plasmid (103 in FIG. 2) are digested with 2 units of HindIII enzyme in 50 μl HindIII buffer (50 mM NaCl; 10 mM Tris.HCl, pH 8; 10 mM MgCl$_2$; and 6 mM β-mercaptoethanol) for 1 hour at 37° C. After phenol/CHCl$_3$ extraction and ethanol precipitation, the DNA is dissolved in 200 μl of a buffer containing 300 mM NaCl, 30 mM sodium acetate at pH 4.25, 1 mM ZnCl$_2$ and 200 units of S1 nuclease (Miles Laboratories). After 1 hour at 15° C., the reaction is stopped by phenol/CHCl$_3$ extraction and ethanol precipitation. The resultant DNA is dissolved in 10 μl T4 DNA ligase buffer containing 20 picomoles phosphorylated BamHI linkers (5'CCGGATCCGG3'', from Collaborative Research) and 2 units T4 DNA ligase. After 16 hours at 4° C., the reaction mixture is heated at 65° C. for 10 minutes to inactivate the ligase and then diluted to 100 μl in BamHI buffer (150 mM NaCl; 6 mM Tris.HCl, pH 8.0; 6 mM MgCl$_2$; and 6 mM β-mercaptoethanol) containing 20 units BamHI enzyme. After 2 hours at 37° C., the mixture is purified on a 1 percent agarose gel.

The gel is stained and the larger fragment (~4.5 kb) is recovered by elution after freezing the gel and then purified by phenol/CHCl$_3$ extraction and ethanol precipitation. The recovered fragment with BamHI cohesive ends is dissolved in 20 μl of T4 DNA ligase buffer containing 1 unit T4 DNA ligase. After 16 hours at 4° C., the DNA is used to transform E. coli RV308. Transformants are selected by resistance to ampicillin (Ap$^r$) at 100 μg/ml and screened for sensitivity to 10 μg/ml tetracycline (Tc$^s$). Several plasmids, prepared by the previously described Birnboim procedure, from colonies which are Ap'Tc' are examined for the absence of a HindIII site and the presence of a single BamHI site. EcoRI and SalI sequential digestion yields a 466 bp and a 305 bp fragment. A plasmid (104 in FIG. 2) with these characteristics is selected and then modified to convert the EcoRI site, located upstream of the lpp promoter, to a HindIII restriction site.

Two micrograms of plasmid (104 in FIG. 2) are digested in 100 µl of EcoRI buffer with 0.2 units of EcoRI for 10 minutes at 37° C. The reaction is stopped by heating for 10 minutes at 65° C., and, after phenol/CHCl$_3$ extraction, the DNA is ethanol precipitated, dissolved in 200 µl of S1 nuclease buffer containing S1 nuclease at 1000 units/ml, and reacted at 12° C. for 1 hour. The reaction is stopped by phenol/CHCl$_3$ extraction and ethanol precipitation. The resultant DNA is resuspended in 10 µl of T4 DNA ligase buffer containing 20 picomoles phosphorylated HindIII linker (5'-CCAAGCTTGG-3', from Collaborative Research) and 2 units of T4 DNA ligase. After 16 hours at 4° C., the mixture is heated for 10 minutes at 65° C., diluted to 150 µl in HindIII buffer containing 10 units HindIII enzyme, incubated for 2 hours at 37° C., and then fractionated on a 1 percent agarose gel. The largest band (equivalent to single cut plasmid) is conventionally recovered and purified, dissolved in 20 µl T4 ligase buffer containing 2 units T4 ligase, incubated 16 hours at 4° C., and then used to transform *E. coli* RV308. Transformants are selected for ampicillin resistance and plasmid isolates conventionally analyzed by restriction enzyme analysis. A plasmid (105 in FIG. 2) with an EcoRI-HindIII fragment of 466 bp is selected and used as the cloning vector for addition of the 3' region of the lpp gene.

About two µg of plasmid (105 in FIG. 3) are digested in 50 µl of SalI restriction buffer (150 mM NaCl; 6 mM Tris.HCl, pH 7.9; 6 mM MgCl$_2$; and 6 mM β-mercaptoethanol) with 2 units of SalI for 1 hour at 37° C. and then diluted to 150 µl in BamHI buffer containing 2 units BamHI. After 1 hour at 37° C., 2.5 units of alkaline phosphatase are added and then incubation is continued for 1 hour at 65° C. The material is phenol/CHCl$_3$ extracted, ethanol precipitated, dissolved in TEN, and used as a cloning vector for the lpp 3' fragment.

To obtain the fragment containing the lpp 3' region, 10 µg of pKEN111 (101 in FIG. 3) are digested in 200 µl of HpaI buffer (20 mM KCl; 10 mM Tris.HCl, pH 7.4; 10 mM MgCl$_2$; and 6 mM β-mercaptoethanol) with 10 units of HpaI for 2 hours at 37° C. After phenol/CHCl$_3$ extraction and ethanol precipitation, the DNA is dissolved in 10 µl T4 DNA ligase buffer containing 20 picomoles phosphorylated SalI linker (5'-GGTCGACC-3', from Collaborative Research) and 2 units T4 DNA ligase and then incubated for 16 hours at 4° C. The ligase is inactivated by heating at 65° C. for 10 minutes. The resultant material is diluted to 100 µl in SalI buffer containing 10 units of SalI and incubated 1 hour at 37° C., and then diluted to 300 µl in PvuII buffer (60 mM NaCl; 6 mM Tris.HCl, pH 7.5; 6 mM MgCl$_2$; and 6 mM β-mercaptoethanol) containing 10 units PvuII restriction enzyme. After 1 hour at 37° C., the DNA is fractionated on a 5 percent polyacrylamide gel.

Approximately 0.5 µg of a 950 bp fragment is recovered, purified and dissolved in TEN. Two-tenths microgram of the fragment is diluted into 20 µl T4 DNA ligase buffer containing 20 picomoles phosphorylated BamHI linker (5'-CCGGATCCGG-3', from Collaborative Research) and 2 units T4 DNA ligase and then incubated for 16 hours at 4° C. The resultant DNA is then heated for 10 minutes at 65° C., diluted to 100 µl in BamHI buffer containing 20 units BamHI, incubated at 37° C. for 2 hours, and then fractionated on a 5 percent polyacrylamide gel to remove excess linker molecules. The resultant 950 bp fragment having BamHI and SalI cohesive ends is conventionally purified and dissolved in 20 µl of T4 DNA ligase buffer containing both 0.2 µg of the BamHI-SalI-digested, alkaline phosphatase-treated plasmid 105 DNA and 2 units T4 DNA ligase. After incubation for 16 hours at 4° C., the DNA is used to transform *E. coli* K12 RV308. Plasmids are prepared from ampicillin resistant transformants and conventionally analyzed for the SalI-BamHI fragment. The desired plasmid (~5.2 kb) is designated pKEN021 (106 in FIG. 3).

Ten micrograms of pKEN021 were digested at 37° C. in 200 µl of XbaI/BamHI buffer (150 mM NaCl; 10 mM Tris.HCl, pH 8; 10 mM MgCl$_2$; and 6 mM β-mercaptoethanol) using 10 units BamHI for 1 hour followed by 10 units of XbaI for an additional hour at 37° C. The desired XbaI-BamHI-digested DNA was then treated with 2.5 units of alkaline phosphatase for 1.5 hours at 65° C., phenol/CHCl$_3$ extracted, collected by ethanol precipitation, and dissolved in 50 µl of TEN for future use (107 in FIG. 3).

B. Construction of Plasmid pNM575

Figure 4:
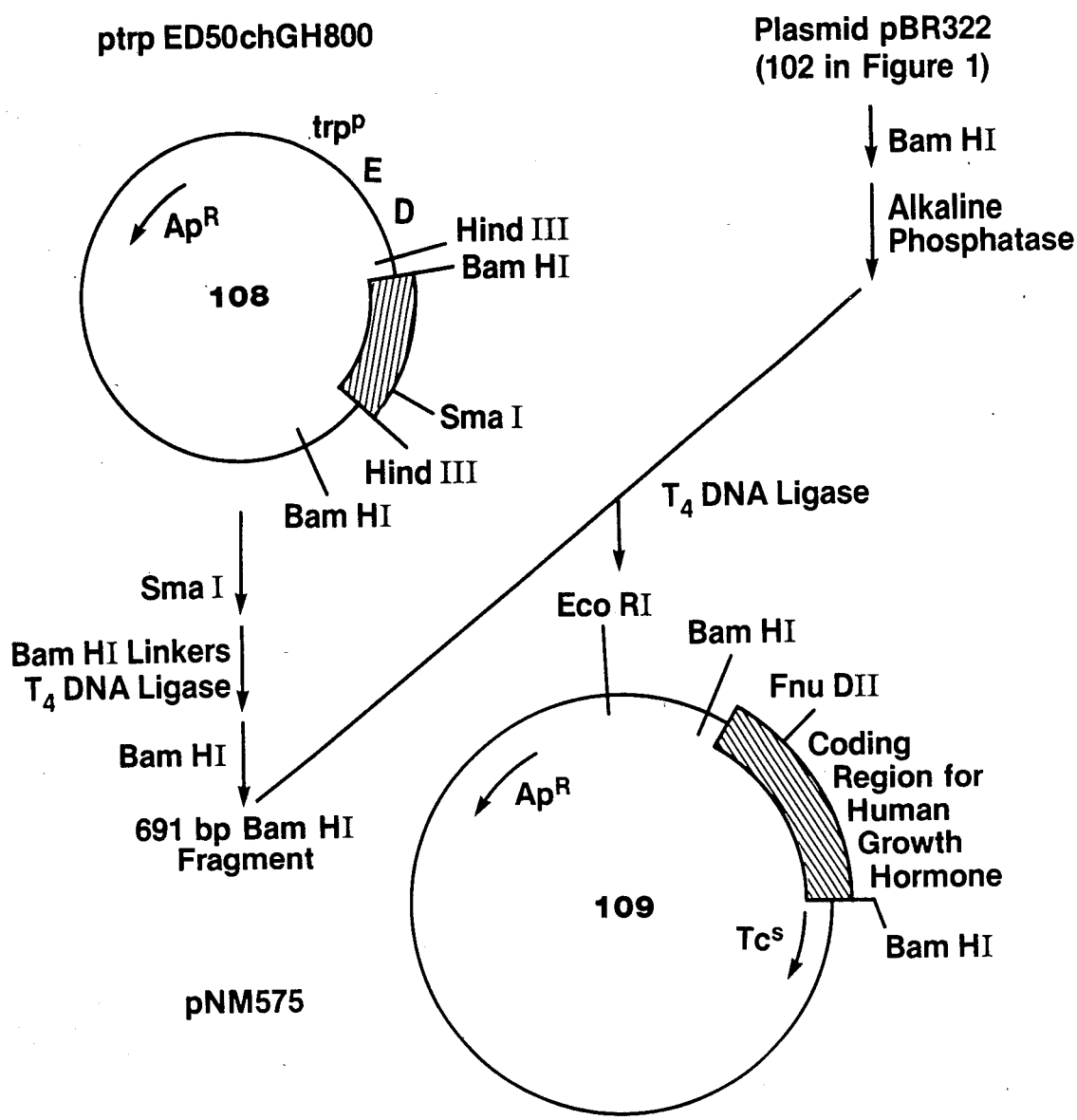

Plasmid ptrpED50chGH800 (108 in FIG. 4), described in Martial et al., 1979, Science 205: 602–607 was used as the source of a DNA fragment containing the coding sequence for a portion of the human growth hormone gene. This fragment can also be constructed synthetically (Itakura et al., 1977 and Crea et al., 1978) or can be obtained using recognized methodology described by Goodman et al., 1979, Methods in Enzymology 68: 75–90, by isolating mRNA coding for human growth hormone from human pituitaries.

The human growth hormone gene portion of plasmid ptrpED50chGH800 contains a unique SmaI restriction site 6 bp downstream from the translation termination codon of the gene. This site was changed to a BamHI site using the following procedure: 6 µg of the plasmid were digested with 6 units of SmaI in 200 µl of SmaI restriction buffer (6 mM Tris.HCl, pH 8.0; 6 mM MgCl$_2$; 20 mM KCl; and 6 mM β-mercaptoethanol) for 1.5 hours at 37° C. After digestion was complete, phenol/CHCl$_3$ extraction was performed and the DNA was recovered by ethanol precipitation and then dissolved in 24 µl of TEN. Forty picomoles of phosphorylated BamHI adapter fragment (Collaborative Research) were added to 0.5 µg (0.2 picomole ends) of the above-digested plasmid in 16 µl of ligase buffer containing 2 units T4 DNA ligase. The mixture was incubated 2 hours at 22° C., 16 hours at 4° C., and then 10 minutes at 65° C. BamHI cohesive termini were generated by conventional digestion with BamHI restriction enzyme.

The enzyme cleaved the linker sequence as well as the BamHI site located at the beginning of the cloned human growth hormone cDNA sequence. This cleavage yielded a 691 bp fragment with cohesive BamHI ends which was separated on a 6 percent polyacrylamide gel and then conventionally recovered. The recovered DNA fragment was ligated (using 2 units T4 DNA ligase in 20 µl of buffer under previously described conditions) with 0.2 µg of BamHI-digested and alkaline phosphatase-treated plasmid pBR322 (102 in FIG. 4). After 16 hours at 4° C., the material was used to transform E. coli strain JA221 (NRRL No. B-15014) in substantial accordance with the transformation procedure of Wensink et al., 1974, Cell 3: 315-325. Transformants were selected on agar plates containing 100 μg/ml ampicillin, and then plasmids were conventionally isolated and identified by restriction enzyme and gel electrophoretic analysis. Desired plasmids, designated as pNM575 (109 in FIG. 4), contain a BamHI fragment of approximately 700 bp and were conventionally amplified for future use.

C. Construction of Plasmid pNM702

The DNA sequence of mature human growth hormone contains one FnuDII site which is 47 bp from the first nucleotide. Twenty-five micrograms of pNM575 were digested in 250 μof BamHI buffer with 25 units of BamHI at 37° C. for 1 hour. The 691 bp fragment with BamHI cohesive termini was conventionally isolated from a 6 percent polyacrylamide gel and purified. After purification of the fragment, one third of it (equivalent to 8 μg of plasmid) was digested in 100 μl of FnuDII buffer (6 mM NaCl; 6 mM Tris.HCl, pH 7.4; 6 mM MgCl$_2$; and 6 mM β-mercaptoethanol) with 2.5 units FnuDII for 1.5 hours at 37° C. Electrophoresis on a 6 percent polyacrylamide gel and standard recovery procedures were used to isolate a 538 bp DNA fragment containing the coding sequence for the last 175 amino acids of the gene followed by a translation stop signal.

Figure 5:
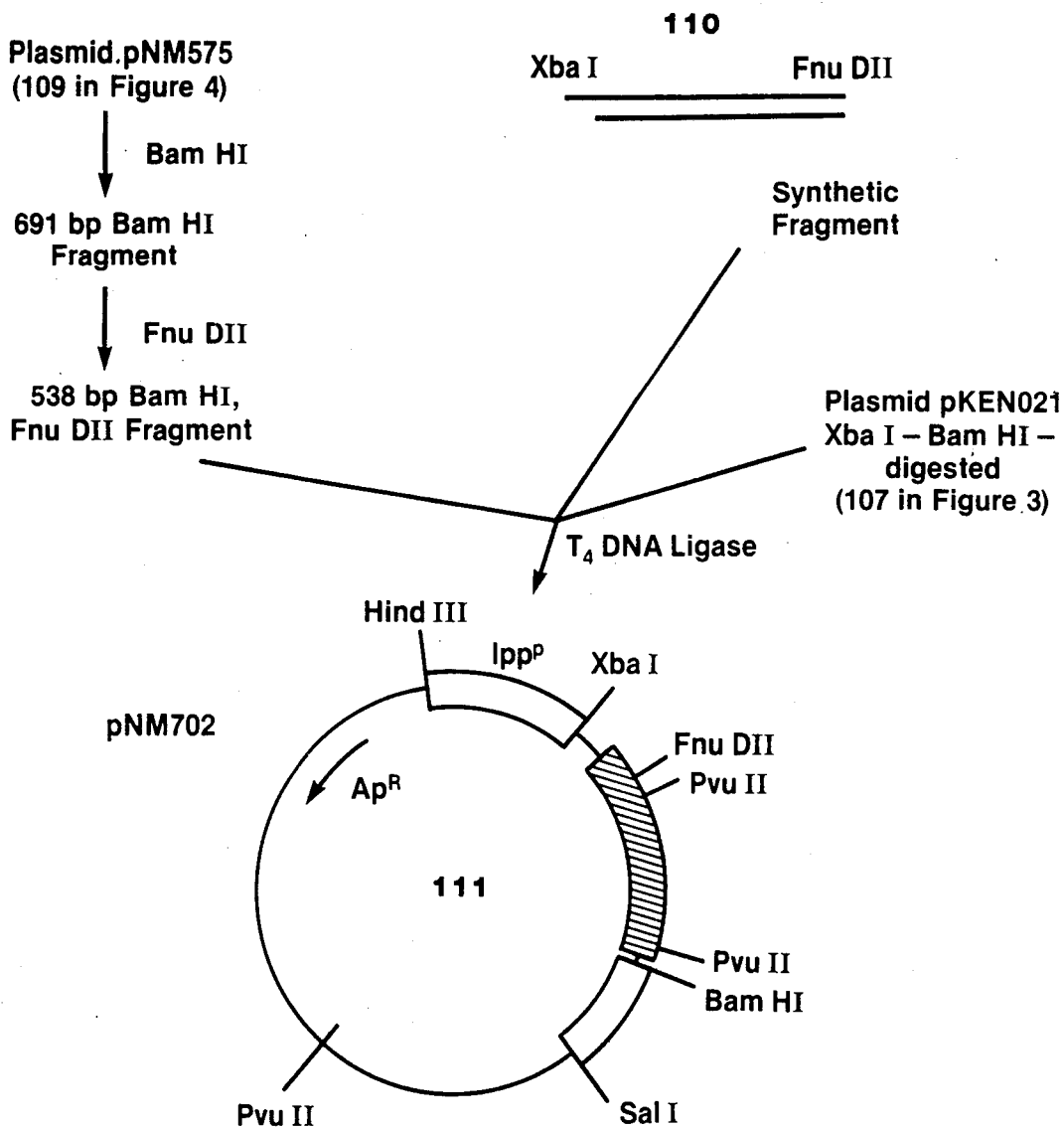

A double stranded DNA fragment (110 in FIG. 5) was synthesized by the phosphotriester method to join the lpp promoter region with the human growth hormone coding region. The double stranded DNA fragment (110 in FIG. 5) has the following sequence:

68: 109-151). The duplex was isolated by preparative gel electrophoresis on 15% polyacrylamide.

(b) 5'-Phosphorylated segment 3 was joined to 5'-phosphorylated segment 4 in the presence of 5'-phosphorylated segment 11 using T4 ligase to form DNA duplex 2 which was purified by 15% polyacrylamide gel electrophoresis.

(c) 5'-Phosphorylated segment 5 was joined to 5'-phosphorylated segment 6 in the presence of 5'-phosphorylated segments 12 and 13 using T4 ligase to form DNA duplex 3 which was purified by 15% polyacrylamide gel electrophoresis.

(d) 5'-Phosphorylated segment 7 was joined to 5'-phosphorylated segment 8 in the presence of 5'-phosphorylated segment 14 and 5'-unphosphorylated segment 15 using T4 ligase to form DNA duplex 4 which was purified by 15% polyacrylamide gel electrophoresis.

(e) The DNA duplexes 2, 3 and 4 then were joined together by T4 ligase to form DNA duplex 5 which was purified by 15% polyacrylamide gel electrophoresis.

(f) 5'-phosphorylated segment 10 and DNA duplex 5 were added, in the presence of T4 ligase, to the DNA duplex 1. The resulting DNA duplex (110 in FIG. 5) was purified by 10% polyacrylamide gel electrophoresis. This DNA duplex then was enzymatically phosphorylated using T4 polynucleotide kinase and [γ-$^{32}$P]-ATP by following established procedure.

The expression plasmid pNM702 (111 in FIG. 5) was constructed by enzymatically joining 0.1 picomole (0.4 μg) of the XbaI-BamHI fragment of plasmid pKEN021 (107 in FIG. 5), 0.025 picomoles synthetic DNA fragment (110 in FIG. 5), and 0.3 picomoles (0.08 μg) of 538

The fragment was prepared by ligating the following single stranded DNA molecules, prepared by recognized phosphotriester methodology:

(1) CTAGAGGGTAT
(2) TAATAATGTTCC
(3) CATTGGATGAT
(4) GATGATAAGTTCC
(5) CAACCATTCCC
(6) TTATCCAGGC
(7) TTTTTGACAACG
(8) CTATGCTCCG
(9) CATTATTAATACCCT
(10) ATGGGAA
(11) CTTATCATCATCATCCA
(12) GGTTGGGAA
(13) GGATAAGGGAAT
(14) GTCAAAAAGCCT
(15) CGGAGCATAGCGTT

Using the above-prepared segments, the T4 ligase catalyzed joining reactions were performed stepwise as described below:

(a) 5'-Unphosphorylated segment 1 was joined to 5'-phosphorylated segment 2 in the presence of 5'-phosphorylated segment 9 using T4 ligase to form DNA duplex 1 (Brown et al., 1979, Methods in Enzymology bp fragment (from 109 in FIG. 5) in 24 μl of ligation buffer using 1.5 units T4 DNA ligase. After incubation for 16 hours at 4° C., the mixture was used to transform E. coli JA221 (NRRL B-15211) as previously described. Transformants were selected on agar plates containing 100 μg/ml amplicillin and were conventionally cultured as a preferred source of the desired expression plasmid.

Expression of human growth hormone was detected by a standard radioimmunoassay procedure (Twomey et al., 1974, Clin. Chem. 20: 389-391) and was determined to be at least 2 million molecules per cell.

D. Construction of Plasmid pNM789

Figure 6:
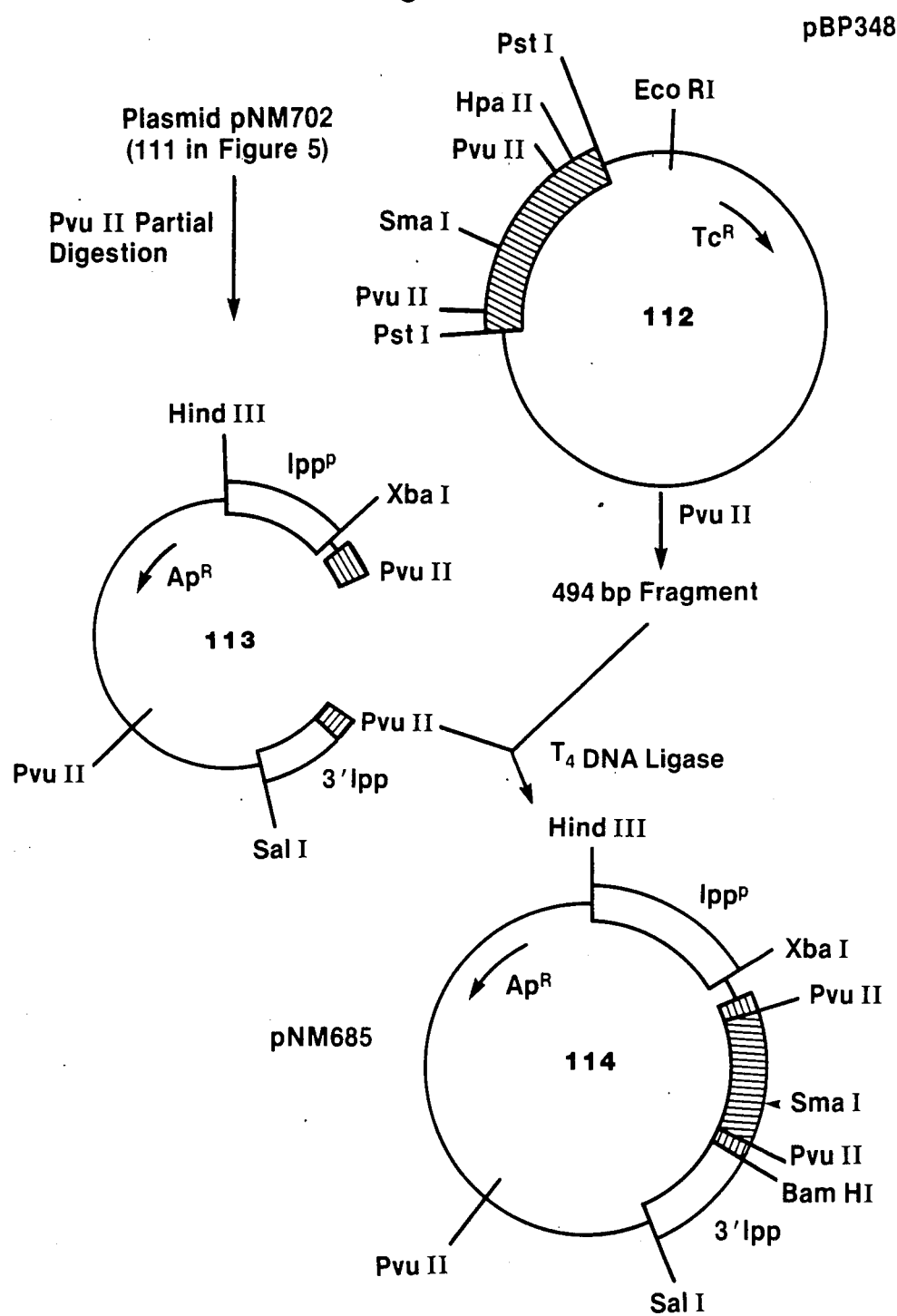

Plasmid pNM702 (111 in FIG. 6), the expression plasmid for human growth hormone, was used as the starting material for construction of a plasmid expressing Met-Phe-Pro-Leu-Asp-Asp-Asp-Asp-Lys-bGH.

Plasmid pBP348 (112 in FIG. 6), described in Miller et al., 1980, J. Biol. Chem. 255: 7521-7524, was used as the source of two DNA fragments containing the coding sequence for a portion of the bovine growth hormone gene. The plasmid contains an 831 bp bovine growth hormone-encoding sequence cloned in the PstI restriction site of pBR322. As an alternative to the method described in Miller et al., 1980, the sequence for bovine growth hormone can be constructed synthetically (Itakura et al., 1977 and Crea et al., 1978) or can also be obtained from messenger RNA isolated from bovine pituitaries by the now routine procedures described by Goodman et al., 1979.

The coding sequences for human growth hormone and bovine growth hormone are very similar and show much homology. Particularly useful in the construction of the expression plasmid for bovine growth hormone were the fragments generated by digestion with the restriction enzyme PvuII. The size of the fragments produced are 497 bp in human growth hormone and 494 bp in bovine growth hormone and the corresponding restriction sites occur in the same reading frames in both sequences.

Ten micrograms of pNM702 (111 in FIG. 6) were partially digested with 1 unit of PvuII in 22 μl of PvuII restriction buffer for 10 minutes at 37° C. After the reaction was stopped by heating at 65° C. for 10 minutes, the DNA was treated with alkaline phosphatase and the fragments separated on a one percent agarose gel. The linear DNA fragment (113 in FIG. 6) of the size that correspond to DNA with the 497 bp PvuII fragment missing (runs slightly faster than single cut plasmid) was conventionally excised, purified, and used in the construction of an intermediate plasmid (114 in FIG. 6).

A 494 bp PvuII fragment of plasmid pBP348 was prepared by digesting 10 μg of the plasmid in 200 μl PvuII buffer containing 10 units of PvuII for 1 hour at 37° C. The fragments were separated on a 6 percent polyacrylamide gel and the desired 494 bp fragment (from 112 in FIG. 6) was conventionally purified.

Intermediate plasmid (114 in FIG. 6) was constructed by reacting 0.2 μg of the plasmid pNM702 PvuII fragment with 0.05 μg of 494 bp fragment in 20 μl of T4 DNA ligase buffer containing 2 units T4 DNA ligase for 16 hours at 4° C. After transformation and selection of transformants for ampicillin resistance, the plasmids were conventionally analyzed for the presence and proper orientation of the 494 by PvuII fragment. Plasmids with a 494 bp PvuII fragment and a 440 bp XbaI-SmaI fragment were selected for use in further constructions.

Figure 7:
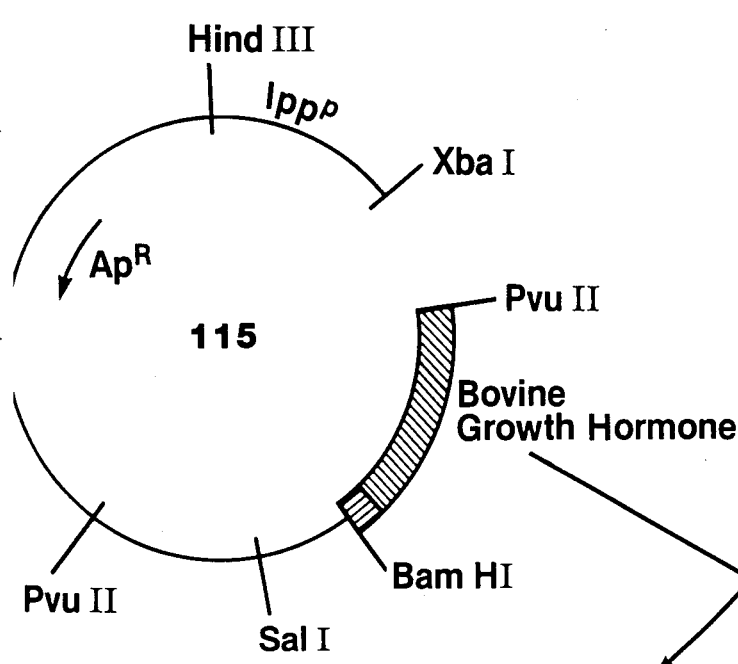
Figure 7:
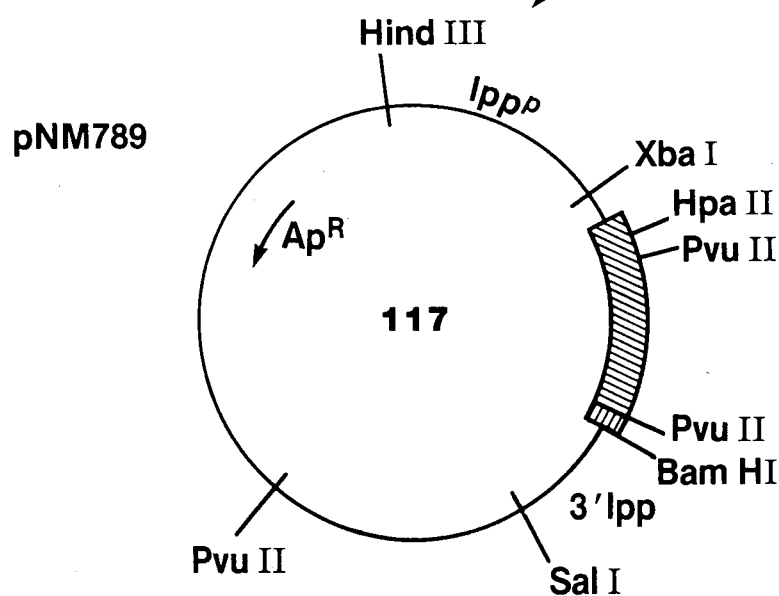

Ten micrograms of the intermediate plasmid (114 in FIG. 7) were digested with 1 unit PvuII in 200 μl PvuII buffer for 5 minutes at 37° C. After heating at 65° C. for 10 minutes, the mixture was electrophoresed on a 1 percent agarose gel and linear DNA having only a single PvuII cut per molecule was recovered and purified. This recovered material (approximately 3 μg) was digested completely with 5 units of XbaI and treated with alkaline phosphatase. The fragments were electrophoresed on a 1 percent agarose gel and the largest fragment (missing the 109 bp fragment between the XbaI and the first PvuII site in human and bovine growth hormone) was conventionally recovered (115 in FIG. 7).

The DNA sequence for the first 23 amino acids (69 bp) of bovine growth hormone up to the first PvuII site contains 2 HpaII restriction sites, the first of which is 23 bp from the first nucleotide of the coding sequence. A 63 bp fragment (116 in FIG. 7) was synthesized by the phosphotriester method and enzymatic ligation. This fragment corresponds to the 19 bp sequence from the XbaI site in the lpp ribosome binding site through the ATG translational start signal followed by the coding sequence for Phe-Pro-Leu-Asp-Asp-Asp-Aso-Lys (24 bp) and 20 nucleotides of the coding sequence of bovine growth hormone (from Phe to the fist HpaII site). The fragment has the following sequence:

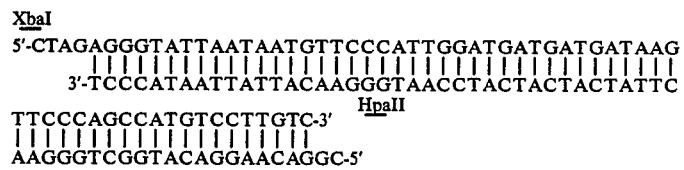

```
    XbaI
5'-CTAGAGGGTATTAATAATGTTCCATTGGATGATGATGATAAG
   ||||||||||||||||||||||||||||||||||||||||||
3'-TCCCATAATTATTACAAGGGTAACCTACTACTACTATTC
                                            HpaII
TTCCAGCCATGTCCTTGTC-3'
|||||||||||||||||||
AAGGGTCGGTACAGGAACAGGC-5'
```

In producing the 63 bp fragment, the following nine segments were prepared:
(1) CTAGAGGGTAT
(2) TAATAATGTTCC
(3) CATTGGATGAT
(4) GATGATAAGTTCC
(5) CAGCCATGTCCTTGTC
(6) ATGGGAACATTATTAATACCCT
(7) TTATCATCATCCA
(8) ATGGCTGGGAAC
(9) CGGACAAGGAC Using the above-prepared segments, the T4 ligase catalyzed joining reactions were performed stepwise as described below:

(a) 5'-Unphosphorylated segment 1 was joined to 5'-phosphorylated segment 2 in the presence of 5'-phosphorylated segmented 6 using T4 ligase to form DNA duplex 1 which was purified by 15% polyacrylamide gel electrophoresis.

(b) 5'-Phosphorylated segments 3, 4 and 5 were joined in the presence of 5'-phosphorylated segments 7 and 8 and 5'-unphosphorylated segment 9 using T4 ligase to form DNA duplex 2 which was purified by 15% polyacrylamide gel electrophoresis.

(c) Duplexes 1 and 2 then were joined by T4 ligase to form a DNA duplex (116 in FIG. 7) which was purified by 15% polyacrylamide gel electrophoresis. This DNA duplex was then enzymatically phosphorylated using T4 polynucleotide kinase and [γ-P$^{32}$]ATP following established procedure.

The DNA fragment of 46 bp, the sequence from the above-described HpaII site to the PvuII site, can either be constructed synthetically or obtained from the original pBP348 plasmid. Accordingly, one hundred micrograms of plasmid pBP348 were digested in 400 μl of PvuII buffer with 50 units of PvuII for 2 hours at 37° C. After phenol extraction and ethanol precipitation, the DNA was dissolved in 400 μl of PstI buffer (100 mM NaCl; 10 mM Tris.HCl, pH 7.5; 10 mM MgCl$_2$; and 6 mM β-mercaptoethanol) with 50 units of PstI for 2 hours at 37° C. The DNA fragments were electrophoresed on a 6 percent polyacrylamide gel and the 135 bp fragment containing the desired 46 bp sequence was recovered and purified by standard procedures. The recovered DNA was subjected to limited digestion by 1 unit of HpaII restriction enzyme in 100 μl HpaII buffer for 10 minutes at 37° C. After heating at 65° C. for 10 minutes, the DNA fragments were run on a 5 percent acrylamide gel (acrylamide:bis ratio 19:1) along with an appropriate size marker. The desired 46 bp fragment yielded by HpaII partial digestion of the 135 bp fragment (from 112 in FIG. 7) was purified by standard procedures.

Two-tenths microgram of the XbaI-PvuII fragment of plasmid vector (115 in FIG. 7), 3.2 picomoles of synthetic 63 bp fragment (116 in FIG. 7), and 0.5 picomoles 46 bp fragment (from 112 in FIG. 7) were incubated in 10 μl ligation buffer with 2 units of T4 DNA ligase for 16 hours at 4° C. The ligation mixture was used to transform *E. coli* JA221, and the resultant transformants, which thus contained the desired plasmid pNM789, were selected by ampicillin resistance. The identity of plasmid pNM789 (117 in FIG. 7) was confirmed by conventionally screening for the presence of both the 494 bp PvuII the 109 bp XbaI-PvuII fragments.

E. Final Construction of Plasmid pNM789B

Figure 8:
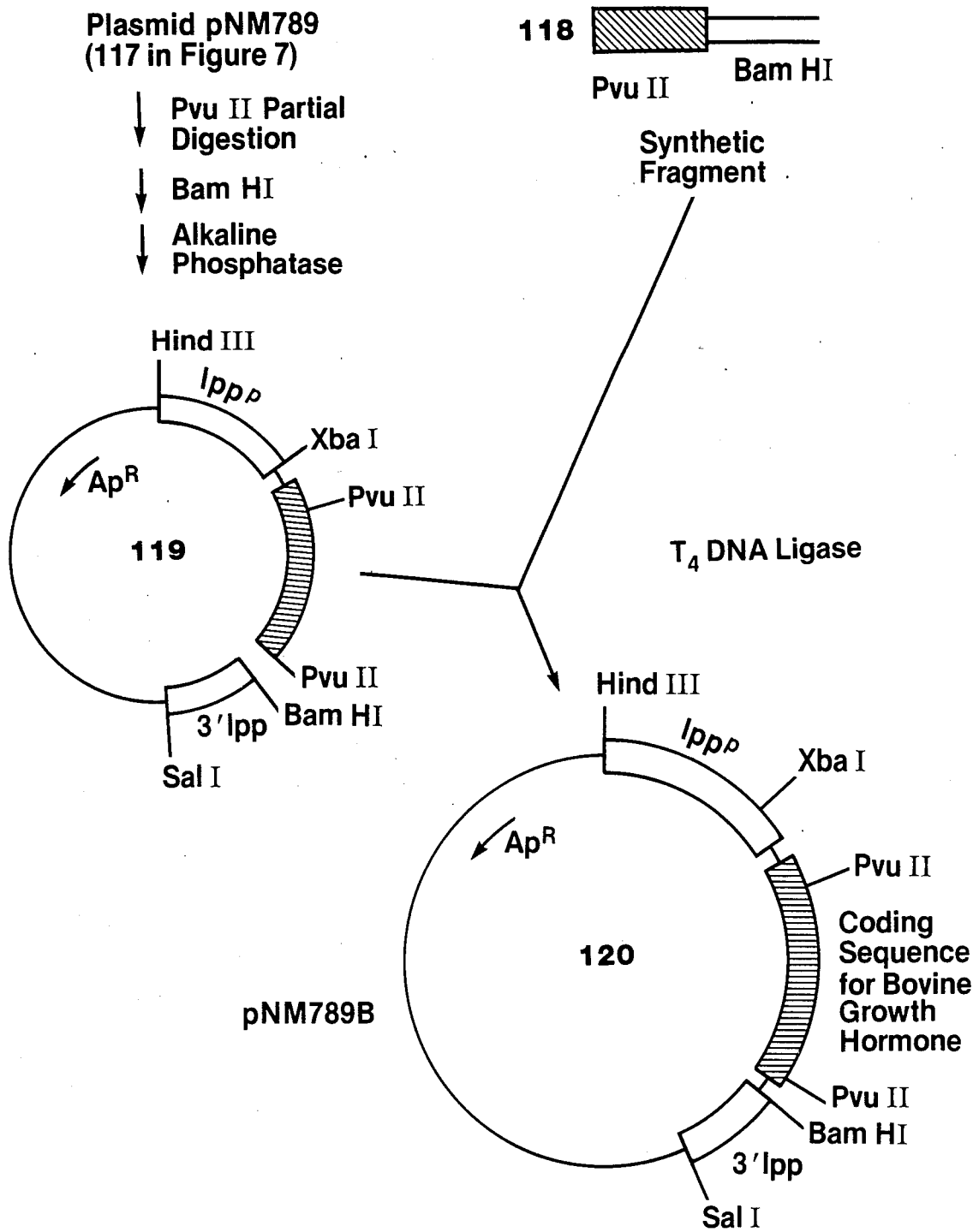
Figure 9:
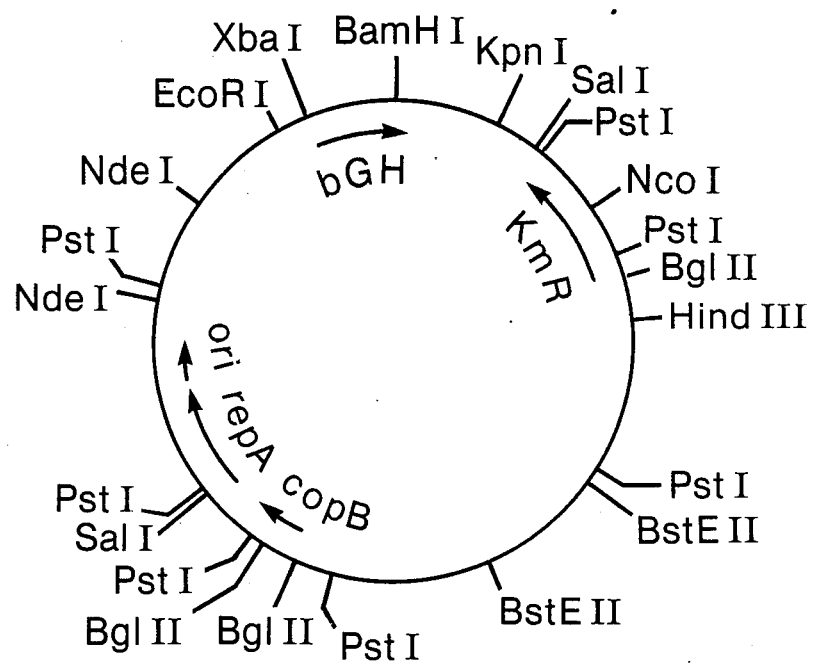
FIG. 9—the restriction site and function map of plasmid pCZ101.

Plasmid pNM789 (117 in FIG. 8) requires one amino acid codon change for complete conversion to bovine growth hormone. This was accomplished by the removal of the 28 bp PvuII to BamHI fragment of PNM789 and replacement with a synthetic double stranded fragment having the following sequence (118 in FIG. 8):

Ten micrograms of pNM789 were digested with 1 unit of PvuII in 200 μl PvuII buffer for 5 minutes at 37° C. After heating 10 minutes at 65° C., the mixture was diluted to 300 μl with the addition of BamHI buffer, digested to completion with 10 units of BamHI, for 1 hour at 37° C., treated with 5 units of alkaline phosphatase, and incubated for 1 hour at 65° C. The DNA fragments were separated on a 1 percent agarose gel, and a DNA fragment (119 in FIG. 8) about the size of linear plasmid pNM789 was conventionally purified. Two-tenths microgram of this fragment was ligated with 5 picomoles of synthetic fragment using 2 units of T4 ligase in 20 μl ligase buffer. The ligation was carried out overnight at 4° C. Following transformation, several plasmids were isolated and screened for the appropriate PvuII (494 bp) and XbaI-BamHI (628 bp) fragments. Plasmids comprising the aforementioned fragments were analyzed by DNA sequencing to determine the transformants harboring the desired plasmid pNM789B (120 in FIG. 8).

EXAMPLE 2

Construction of Plasmid pCZ101 and *E. coli* K12 RV308/pCz101

A. Isolation of Plasmid pIM-I'-A3

The bacterium *E. coli* K12/pIM-I'-A3 (NRRL B-15733) was cultured in TY broth (1% tryptone, 0.5% yeast extract, 0.5% sodium chloride, and pH 7.4) with 50 μg/ml of kanamycin at 25° C. according to conventional microbiological procedures. After the culture was diluted 1:10 into fresh broth and after 3 hours incubation at 37° C., about 1.5 ml of the culture was transferred to a 1.5 ml Eppendorf tube and centrifuged for about 15 seconds. Unless otherwise indicated, all the manipulations were done at ambient temperature. The resultant supernatant was carefully removed with a fine-tip aspirator, and the cell pellet was resuspended in about 100 μl of freshly prepared lysozyme solution which contained 2 mg/ml lysozyme, 50 mM glucose, 10 mM EDTA, and 25 mM Tris.HCl at pH 8. About 200 μl of alkaline SDS (sodium dodecyl sulfate) solution (0.2N NaOH and 1% SDS) were added and the tube was gently inverted and then kept at 0° C. until lysis was complete (~5 minutes). Next, about 150 μl of 3M sodium acetate were added, and the contents of the tube mixed gently by inversion.

The tube was maintained at 0° C. of at least 60 minutes and then centrifuged for 15 minutes to yield an almost clear supernatant. The supernatant was transferred to a second centrifuge tube to which 3 volumes of cold 100% ethanol were added. After the tube was held on dry ice-ethanol for 5 minutes, the resultant precipitate was collected by centrifugation, and the supernatant was removed by aspiration. The collected pellet was dissolved in 100 μl of TE (10 mM Tris.HCl, pH 8.0 and 1 mM EDTA) and constituted the desired plasmid pIM-I'-A3 DNA.

B. XbaI-BamHI Digestion of Plasmid pNM789B and generation of the ~0.6 kb XbaI-BamHI Fragment About 5 μg of plasmid pNM789B DNA in 50 μl Hi Salt buffer* were incubated with 10 units each of BamHI and XbaI restriction enzymes at 37° C. for about 1 hour. After the addition of 5 μl of 3M sodium acetate at pH 7.0, the DNA was precipitated with 2 volumes of 100% ethanol. The desired DNA digest was dissolved in 100 μl of TE buffer and stored at 0° C. for future use.
*Hi Salt buffer was conventionally prepared with the following composition:
 100 mM NaCl
 20 mM Tris.HCl, pH 8.0
 10 mM MgCl₂
 5 mM β-mercaptoethanol

C. XbaI-BamHI Digestion of Plasmid pIM-I'-A3

The desired digestion was carried out in substantial accordance with the procedure of Example 2B except that plasmid pIM-I'-A3, rather than plasmid pNM789B, was used. The desired DNA was dissolved in about 100 μl of TE buffer and stored at 0° C. for future use.

D. Ligation and Transformation

About 1 μg of the plasmid pIM-I'-A3 XbaI-BamHI digest, 1 μg of the plasmid pNM789B XbaI-BamHI digest, 40 μl water, 5 μl (5 mM) ATP, 5 μl ligation mix*, and 5 units T4 DNA ligase were mixed together and incubated at 20° C. for about 2 hours. After incubation at 65° C. for 2 minutes followed by cooling on ice, the resultant ligation mixture was used to transform, in substantial accordance with the transformation procedure of Wensink, 1974, Cell 3:3315, *E. coli* K12 RV308 on TY plates (1% tryptone, 0.5% yeast extract, 0.5% sodium chloride, 1.5% agar, pH 7.4) containing 50 μg/ml of kanamycin. Bacterial strain *E. coli* K12 RV308 has been deposited and made part of the permanent stock culture collection of the Northern Regional Research Laboratory, Peoria, Ill., from which it is available to the public under the accession number NRRL B-15624.
*Ligation mix can be prepared with the following composition:
 500 mM Tris.HCl, pH 7.8
 200 mM Dithiothreitol
 100 mM MgCl₂

Some of the resultant transformants, as conventionally shown by agarose gel electrophoresis (Maniatis et

17 al., 1982) and other tests, contained only the desired ~10.8 kb plasmid. Such a transformant, herein designated as *E. coli* K12 RV308/pCZ101, was selected, plated on TY agar containing appropriate antibiotics, and then cultured using conventional microbiological techniques. The resultant cells were used to isolate plasmid pCZ101 in substantial accordance with the procedure of Example 2A.

EXAMPLE 3

Construction of Plasmid pCZ103 and *E. coli* K12 RV308/pCZ103

Plasmid pCZ101 contains two BstEII restriction enzyme recognition sites separated by 900 bp of DNA. Deletion of this 900 bp BstEII fragment removes DNA that possibly encodes a transposase and results in plasmid pCZ103.

Fifty μg of plasmid pCZ101 were incubated at 60° C. for two hours in the presence of 100 Units BstEII in a buffer that was 150 mM NaCl, 6 mM Tris-HCl (pH 7.9), 6 mM MgCl₂, and 6 mM 2-mercaptoethanol. The desired ~9.9 kb BstEII restriction fragment was conventionally separated and isolated from the other reaction products by agarose gel electrophoresis and then dissolved in about 100 μl of TE buffer and stored at 0° C. for future use.

18 herein designated as *E. coli* K12 RV308/pCZ103, was selected, plated on TY agar containing appropriate antibiotics, and then cultured using conventional microbiological techniques. The resultant cells were used to isolate plasmid pCZ103 in substantial accordance with the procedure of Example 2A.

EXAMPLE 4

Construction of the Expression Control Sequence

The desired expression control sequences were synthesized with a Model 380A DNA Synthesizer, marketed by Applied Biosystems. Other DNA synthesizing instruments are known in the art and would function equally well for the construction. Alternatively, the DNA segments may be conventionally synthesized by the improved, modified phosphotriester method in substantial accordance with the teaching of Hsiung et al., 1983. The aforementioned synthesis method is also specifically illustrated in Example 1. The expression control sequences are synthesized from single stranded DNA segments; since the present sequences are related to one another, many of the segments were used in the construction of each of the four expression control sequences.

The four expression control sequences of the present invention are listed below in A–D.

```
A  5'-AATTCCATCAAAAAAATATTGACAACATATCATCGAACTAGTTAACTAGTACGCAAG
      ||||||||||||||||||||||||||||||||||||||||||||||||||||||||
   3'-GGTAGTTTTTTTATAACTGTTGTATAGTAGCTTGATCAATTGATCATGCGTTC
   TTCACGT-3'
   |||||||
   AAGTGCAGATC-5'

B  5'-AATTCCATCAAAAAAATATTGACAACATATCATCGAACTAGTTAACTAGTACGCAAG
      ||||||||||||||||||||||||||||||||||||||||||||||||||||||||
   3'-GGTAGTTTTTTTATAACTGTTGTATAGTAGCTTGATCAATTGATCATGCGTTC
   TTCACGTAAAAAGGGTAT-3'
   ||||||||||||||||||
   AAGTGCATTTTTCCCATAGC-5'

C  5'-AATTCCATCAAAAAAATATTGACAACATATCATCGAACTAGTATAATAGTACGCAAG
      ||||||||||||||||||||||||||||||||||||||||||||||||||||||||
   3'-GGTAGTTTTTTTATAACTGTTGTATAGTAGCTTGATCATATTATCATGCGTTC
   TTCACGT-3'
   |||||||
   AAGTGCAGATC-5'

D  5'-AATTCCATCAAAAAAATATTGACAACATATCATCGAACTAGTATAATAGTACGCAAG
      ||||||||||||||||||||||||||||||||||||||||||||||||||||||||
   3'-GGTAGTTTTTTTATAACTGTTGTATAGTAGCTTGATCATATTATCATGCGTTC
   TTCACGTAAAAAGGGTAT-3'
   ||||||||||||||||||
   AAGTGCATTTTTCCCATAGC-5'
```

About 5 μl of the ~9.9 kb BstEII restriction fragment of plasmid pCZ101 were ligated and the resultant plasmid used to transform *E. coli* RV308 in substantial accordance with the teaching of Example 2D. Some of the resultant transformants, as conventionally shown by agarose gel electrophoresis and other tests, contained only the desired 9.9 kb plasmid. Such a transformant, wherein A is deoxyadenyl, G is deoxyguanyl, C is deoxycytidyl, and T is thymidyl.

The single stranded DNA segments used to construct each control sequence are listed in the following Table and are listed below the letter designating the entire expression control sequence. The segments are oriented in the 5' to 3' direction.

TABLE I

|   | Control Sequence A | Control Sequence B |
|---|---|---|
| 1 | AATTCCATCAAAAAAATA | AATTCCATCAAAAAAATA |
| 2 | TTGACAACATATCATCGA | TTGACAACATATCATCGA |
| 3 | ACTAGTTAACTAGTACG | ACTAGTTAACTAGTACG |
| 4 | CAAGTTCACGT | CAAGTTCACGTAAAAAGGGTAT |
| 5 | GTCAATATTTTTTTGATGG | GTCAATATTTTTTTGATGG |
| 6 | CTAGTTCGATGATATGTT | CTAGTTCGATGATATGTT |
| 7 | AACTTGCGTACTAGTTAA | AACTTGCGTACTAGTTAA |
| 8 | CTAGACGTG | CGATACCCTTTTTACGTG |

|   | Control | Control |

TABLE I-continued

| | Sequence | Sequence D |
|---|---|---|
| 1 | AATTCCATCAAAAAAATA | AATTCCATCAAAAAAATA |
| 2 | TTGACAACATATCATCGA | TTGACAACATATCATCGA |
| 3 | ACTAGTATAATAGTACG | ACTAGTATAATAGTACG |
| 4 | CAAGTTCACGT | CAAGTTCACGTAAAAAGGGTAT |
| 5 | GTCAATATTTTTTTGATGG | GTCAATATTTTTTTGATGG |
| 6 | CTAGTTCGATGATATGTT | CTAGTTCGATGATATGTT |
| 7 | AACTTGCGTACTATTATA | AACTTGCGTACTATTATA |
| 8 | CTAGACGTG | CGATACCCTTTTTACGTG |

After phosphorylating all of the segments except 1 and 8, the segments were annealed, ligated, and the desired expression control sequence isolated from the reaction mix by polyacrylamide gel electrophoresis. Since the control sequences were synthesized with overlaps characteristic of EcoRI, XbaI, or ClaI cleavage, the control sequences were immediately ready for use in subsequent constructions.

EXAMPLE 5

Construction of Plasmid pCLTbGH29 And E coli RV308/pCLTbGH29

A. Construction of the ~9.3 kb BamHI-EcoRI Restriction Fragment of Plasmid pCZ103

Fifty μg of plasmid pCZ103 were incubated at 37° C. for two hours with 100 Units BamHI in 100 μl of reaction buffer composed of 150 mM NaCl, 6 mM Tris-HCl (pH 7.9), and 6 mM MgCl$_2$. After two hours, the reaction was diluted to 300 μl; the buffer was changed to 100 mM Tris-HCl (pH 7.5), 50 mM NaCl, and 5 mM MgCl$_2$; 100 Units EcoRI were added to the reaction; and the reaction was then incubated another two hours at 37° C. The desired ~9.3 kb EcoRI-BamHI restriction fragment was separated from the other reaction products by agarose gel electrophoresis and then purified in substantial accordance with the teaching of Example 1. The purified fragment obtained was dissolved in TE buffer to a final concentration of 1 μg/μl and stored at 0° C. for future use.

B. Construction of the ~0.6 kb BamHI-HgiAI Restriction Fragment of Plasmid pCZ103

Fifty μg of plasmid pCZ103 were incubated for two hours at 37° C. with 100 Units each of restriction enzymes BamHI and HgiAI. The reaction buffer was 200 mM NaCl, 10 mM Tris-HCl (pH 8.0), 10 mM MgCl$_2$, and 10 mM 2-mercaptoethanol. The reaction volume was 200 μl. After the reaction was complete, the desired ~0.6 kb BamHI-HgiAI restriction fragment was separated from the other reaction products by agarose gel electrophoresis in substantial accordance with the teaching of Example 1. The purified fragment obtained was dissolved in TE buffer to a concentration of 1 μg/μl and stored at 0° C. for future use.

C. Construction of the DNA Linker Sequence

The desired DNA linker sequence:

```
5'-CTAGAGGGTATTAATA ATG TTT CCA GCT ATG TCT CTA TCT
   ||||||||||||||||  |||  |||  |||  |||  |||  |||  |||  |||
3'-TCCCATAATTAT TAC AAA GGT CGA TAC AGA GAT AGA
   GGT CTG TTT GCC AAC GCT GTGCT-3'
   |||  |||  |||  |||  |||  |||  |
   CCA GAC AAA CGG TTG CGA C-5'
``` was conventionally synthesized by the improved, modified phosphotriester method of Hsiung et al., 1983. The aforementioned synthesis method is also specifically illustrated in Example 1.

D. Ligation and Transformation

One μg of each of the DNA fragments prepared in Examples 5A and 5B and four picomoles each of the linker prepared in Example 5C and of expression control sequence A of Example 4 were ligated and then used to transform E. coli RV308 in substantial accordance with the teaching of Example 2D, except that the ligation reaction was incubated at 4° C. for 16 hours instead of at 20° C. for 2 hours.

Figure 11:
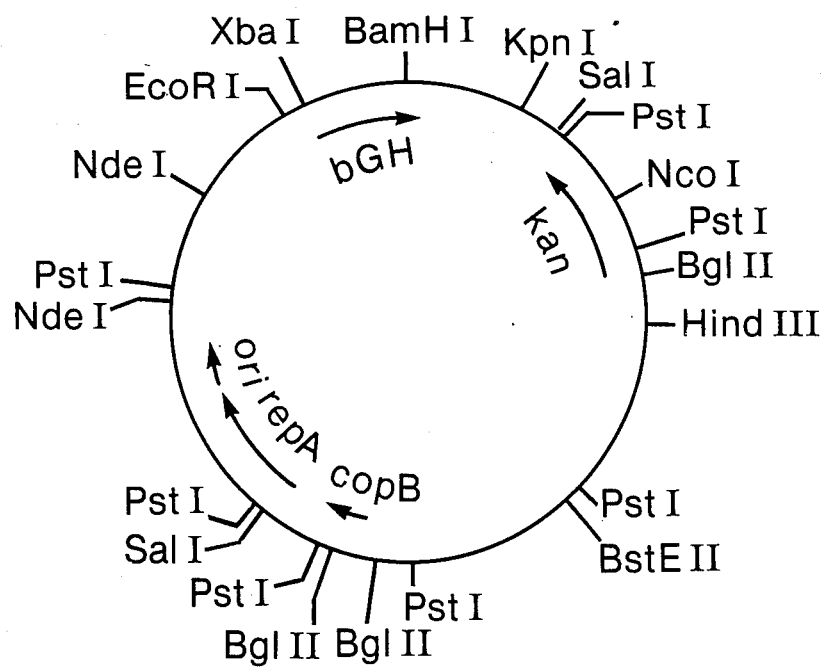
FIG. 11—the restriction site and function map of plasmid pCLTbGH29.

Several of the transformants were shown, by restriction enzyme analysis of their plasmid DNA, to contain only plasmid pCLTbGH29. Such an E. coli RV308/pCLTbGH29 transformant expresses the abovedefined MET-bGH to a level constituting ~30% of the total cell protein when grown at 37° C., the permissive temperature for the runaway replicon encoded on the plasmid. When grown at the restrictive temperature for the replicon, ~25° C., in the presence of tryptophan, plasmid pCLTbGH29 expresses very low levels of MET-bGH. This is because the expression control sequence present on plasmid pCLTbGH29 comprises an intact tryptophan operator recognition sequence. The presence of tryptophan does not significantly affect expression of MET-bGH from plasmid pCLTbGH29 at 37° C. A restriction site and function map of plasmid pCLTbGH29 is presented in FIG. 11 of the accompanying drawings.

EXAMPLE 6

Construction of Plasmid pCLTbGH37 and E. coli RV308/pCLTbGH37

These constructions were accomplished by substantial accordance with the procedure of Example 5. Thus, plasmid pCLTbGH37 is constructed by using the EcoRI-XbaI expression control sequence C of Example 4, in place of control sequence A, in the procedure of Example 5. Plasmid pCLTbGH37 does not comprise a tryptophan operator recognition sequence. An E. coli RV308/pCLTbGH37 transformant was identified by restriction enzyme analysis of its plasmid DNA; expression levels obtained with this transformant are similar to those obtained with E. coli RV308/pCLTbGH29.

EXAMPLE 7

Construction of Plasmid pCLTbGH51 and E. coli RV308/pCLTbGH51

A. Isolation of Plasmid pCZ103 Restriction Fragments

The ~9.3 kb EcoRI-BamHI and ~0.6 kb BamHI-HgiAI restriction fragments of plasmid pCZ103 isolated and purified in Example 5A and 5B, respectively, are also used in the construction of plasmids pCLTbGH51 and pCLTbGH64.

B. Construction of the DNA Linker Sequence

The desired DNA linker sequence:

```
5'-CGATA ATG GAT TTT CCG GCT ATG TCT CTG TCC GGC CTG
   ||||| ||| ||| ||| ||| ||| ||| ||| ||| ||| ||| |||
3'-TAT TAC CTA AAA GGC CGA TAC AGA GAC AGG CCG GAC

TTT GCC AAC GCT GTGCT-3'
||| ||| ||| ||| |
AAA CGG TTG CGA C-5'
``` was conventionally synthesized by the improved, phosphodiester method of Husing et al., 1983. The aforementioned synthesis method is also specifically illustrated in Example 1.

C. Ligation and Transformation

One μg each of the restriction fragments prepared in Examples 5A and B and four picomoles of the linker sequence prepared in Example 7B were ligated to four picomoles of expression control sequence B prepared in Example 4 and then used to transform E. coli RV308 in substantial accordance with the teaching of Example 5D.

Figure 10:
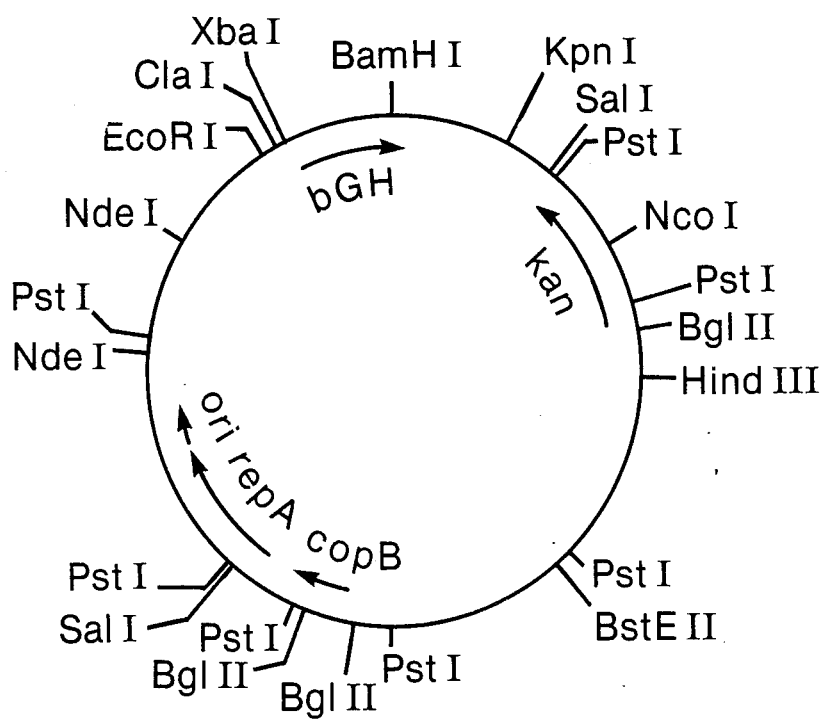
FIG. 10—the restriction site and function map of plasmid pCLTbGH51.

Plasmid pCLTbGH51, like plasmid pCLTbGH29, contains the tryptophan operator recognition sequence. An E. coli RV308/pCLTbGH51 transformant will express the above-defined MET-ASP-bGH at levels approaching 30% of the total cell protein when incubated at the permissive temperature of the runaway replicon. A restriction site and function map of plasmid pCLTbGH51 is presented in FIG. 10 of the accompanying drawings.

EXAMPLE 8

Construction of Plasmid pCLTbGH64 and E. coli RV308/pCLTbGH64

Plasmid pCLTbGH64 and transformant E. coli RV308/pCLTbGH64 were constructed by using expression control sequence D of Example 4, in place of control sequence B, in the procedure of Example 7. Plasmid pCLTbGH64 does not comprise the tryptophan operator recognition sequence. The E. coli RV308/pCLTbGH64 transformant expresses MET-ASP-bGH at levels approaching 30% of the total cell protein when grown at the permissive temperature of the runaway replicon encoded on the plasmid.

We claim:

1. The expression control sequence:

```
5'-GAATTCCATCAAAAAAATATTGACAACATATCA
   |||||||||||||||||||||||||||||||||
3'-CTTAAGGTAGTTTTTTTATAACTGTTGTATAGT

TCGAACTAGT           TAGTACGCAAGTTCACGT
||||||||||-R-||||||||||||||||||||-R₁
AGCTTGATCA           ATCATGCGTTCAAGTGCA
``` wherein A is deoxyadenyl, G is deoxyguanyl, G is deoxycytidyl, T is thymidyl,
R can independently be

```
5'-TAAC-3'         5'-ATAA-3'
   ||||      or      ||||     , and
3'-ATTG-5'         3'-TATT-5'
```

R¹ can independently be

```
5'-CTAGA-3'        5'-AAAAAGGGTATCGAT-3'
   |||||     or       |||||||||||||||
3'-GATCT-5'        3'-TTTTTCCCATAGCTA-5'
```

2. A selectable and autonomously replicating recombinant DNA cloning vector comprising an expression control sequence of claim 1.

3. The vector of claim 2 which is a plasmid comprising a selectable marker and a replicon.

4. The plasmid of claim 3 which further comprises a structural gene encoding a functional polypeptide, and wherein said expression control sequence is positioned to control expression of said structural gene, provided that when R₁ is

```
5'-CTAGA-3'
   |||||
3'-GATCT-5'
``` a translational-activating sequence is positioned between R₁ and the structural gene.

5. The plasmid of claim 4, wherein the structural gene encodes a protein.

6. The plasmid of claim 5 that is plasmid pCLTbGH29.

7. The plasmid of claim 5 that is plasmid pCLTbGH37.

8. The plasmid of claim 5 that is plasmid pCLTbGH51.

9. The plasmid of claim 5 that is plasmid pCLTbGH64.

10. The plasmid of claim 5, wherein said protein is selected from the group consisting of human growth hormone, pig growth hormone, bovine growth hormone, avian growth hormone, growth hormone releasing factor, proinsulin, insulin A chain, insulin B chain, Factor VIII, tissue plasminogen activator, IGFI, IFGII, interleukin I, and interleukin II.

11. The plasmid of 10, wherein said protein is human growth hormone.

12. The plasmid of claim 10, wherein said protein is tissue plasminogen activator.

13. The plasmid of claim 10, wherein said protein is proinsulin.

14. A host cell transformed with a recombinant DNA cloning vector that comprises the expression control sequence:

```
5'-GAATTCCATCAAAAAAATATTGACAACATATCA
   |||||||||||||||||||||||||||||||||
3'-CTTAAGGTAGTTTTTTTATAACTGTTGTATAGT
```

```
TCGAACTAGT   TAGTACGCAAGTTCACGT
||||||||||-R-||||||||||||||||||-R₁
AGCTTGATCA   ATCATGCGTTCAAGTGCA
``` wherein A is deoxyadenyl, G is deoxyguanyl, C is deoxycytidyl, T is thymidyl,

R can independently be

```
5'-TAAC-3'        5'-ATAA-3'
   ||||     or      ||||     , and
3'-ATTG-5'        3'-TATT-5'
```

R₁ can independently be

```
5'-CTAGA-3'        5'-AAAAAGGGTATCGAT-3'
   |||||    or        |||||||||||||||
3'-GATCT-5'        3'-TTTTTCCCATAGCTA-5'
```

15. The host cell of claim 14 that is *E. coli*.
16. The host cell of claim 15 that is *E. coli* K12 RV308.
17. The host cell of claim 16 that is *E. coli* K12 RV308/pCLTbGH29.
18. The host cell of claim 16 that is *E. coli* K12 RV308/pCLTbGH37.
19. The host cell of claim 16 that is *E. coli* K12 RV308/pCLTbGH51.
20. The host cell of claim 16 that is *E. coli* K12 RV308/pCLTbGH64.

* * * * *